(12) United States Patent
Miyamura

(10) Patent No.: US 8,490,502 B2
(45) Date of Patent: Jul. 23, 2013

(54) LIQUID SAMPLE ANALYZER

(75) Inventor: Kazuhiro Miyamura, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 245 days.

(21) Appl. No.: 13/023,149

(22) Filed: Feb. 8, 2011

(65) Prior Publication Data

US 2011/0192219 A1 Aug. 11, 2011

(30) Foreign Application Priority Data

Feb. 8, 2010 (JP) .................. 2010-025941

(51) Int. Cl.
*G01N 35/00* (2006.01)
(52) U.S. Cl.
USPC ...................................... 73/864.81
(58) Field of Classification Search
None
See application file for complete search history.

(56) References Cited

U.S. PATENT DOCUMENTS

| 6,822,180 | B2* | 11/2004 | Fujii et al. | 209/128 |
| 7,463,158 | B2* | 12/2008 | Hatch et al. | 340/627 |
| 2010/0192701 | A1* | 8/2010 | Schmitt et al. | 73/861.24 |
| 2012/0202277 | A1* | 8/2012 | Wagner et al. | 435/288.7 |

FOREIGN PATENT DOCUMENTS

JP 2007-017302 A 1/2007

* cited by examiner

*Primary Examiner* — Robert R Raevis
(74) *Attorney, Agent, or Firm* — Alleman Hall McCoy Russell & Tuttle LLP

(57) ABSTRACT

The present invention removes an air bubble attaching to a detection part arranged in a concave portion on a wall surface in a flow path or an air bubble generated in the vicinity without requiring an external driving force, in a simple configuration. Specifically, the present invention includes: a liquid sample flow path for circulating a liquid sample; a detection part contained and arranged in a stepwise concave portion formed on an inner wall surface of the liquid sample flow path; and a projection part provided at a position facing to the stepwise concave portion on an inner wall surface of the liquid sample flow path, for generating a turbulent flow on a front side of an opening of the stepwise concave portion.

4 Claims, 12 Drawing Sheets

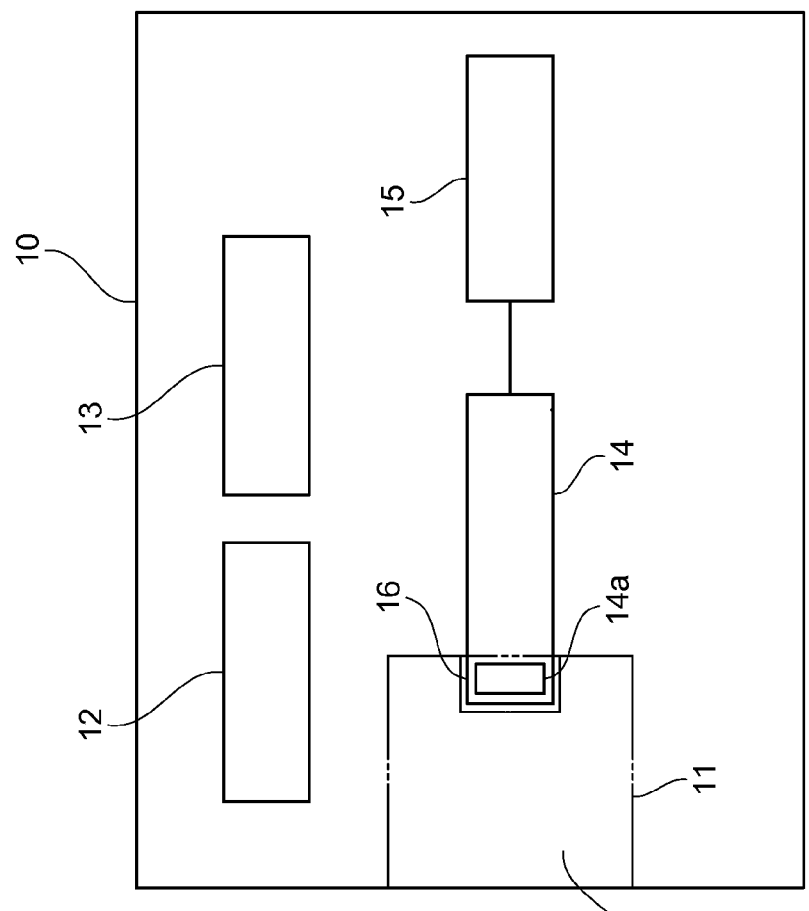
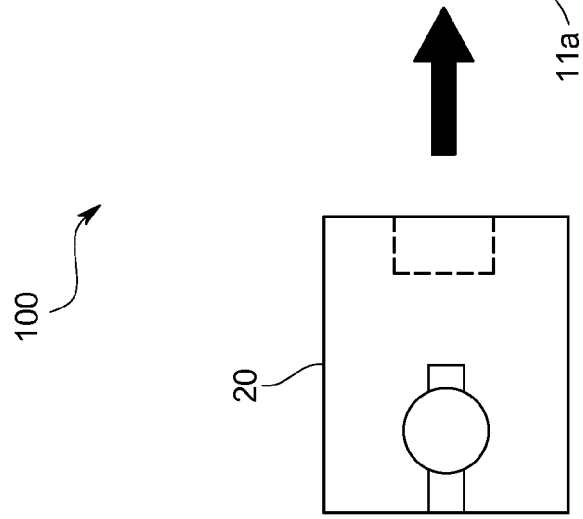
Fig.1

LIQUID SAMPLE ANALYZER

TECHNICAL FIELD

The present invention relates to a liquid sample analyzer for analyzing a liquid sample such as blood.

BACKGROUND

In this type of a liquid sample analyzer, as described in JP2007-17302A, there is a cartridge detachably attached to a measurement main body. This cartridge includes a flow path for flowing a diluted sample blood, which serves as a liquid sample, and a detection part provided in the flow path to measure the sample blood.

In one specific configuration, the cartridge includes: a first substrate, which forms a concave groove on the surface; a second substrate, which configures the flow path by covering an opening part of the concave groove when adhered to the first substrate and which forms a detection part, the detection part in contact with the sample blood and a lead line; and an adhesive sheet for joining the first substrate and the second substrate. Further, the adhesive sheet is configured to almost entirely cover a surface of the first substrate except for a part corresponding to a place where the detection part is formed. As the cartridge is configured in this manner, the detection part is contained and arranged in a stepwise concave portion formed by the adhesive sheet and the second substrate in the flow path (see FIG. 12).

In the cartridge, when the sample blood flows in the flow path, the sample blood experiences surface tension from a flow path wall surface (FIG. 12, at (a)). As such, the flow of sample blood is blocked at an upper-stream side corner part of the stepwise concave portion configured by the adhesive sheet and the second substrate, while the sample blood flows on an inner surface of the concave groove of the first substrate (FIG. 12, at (b)). In this manner, an air layer is formed in the vicinity of the detection part and the sample blood directly flows on the inner surface of the concave portion (FIG. 12, at (c)), and thereby causes a problem that the sample blood contacts a lower-stream side corner part of the adhesive sheet and an air bubble is formed in the vicinity of the detection part (see FIG. 12, at (d)). When the air bubble has been formed in the vicinity of the detection part as described above, there is a problem that a signal from the detection part is varied or the detection part and the liquid sample are insulated from each other, deteriorating accuracy of a measurement.

In addition to the case of forming the air bubble due to the air layer, as described above, an air bubble included in the sample blood has a tendency to stay in the stepwise concave portion formed by the adhesive sheet and the second substrate, and as a result, there is a problem that the air bubble adheres to the detection part. When the air bubble has adhered to the detection part as described above, there is a problem that a signal from the detection part is varied or the detection part and the liquid sample are insulated from each other, deteriorating accuracy of a measurement.

To address this, in general, as a method for removing the air bubble that adhered to the detection part, it can be considered to make the air bubble difficult to adhere to the detection part due to arrangement of a position of the detection part itself on a bottom surface or right and left surfaces of the flow path or in a state of being suspended in the flow path.

However, since the only force applied to the air bubble is buoyancy, there is a problem that once the air bubble attaches to the detection part, removal is difficult. In addition, in a case where the detection part is formed on the upper surface (a case of FIG. 12), there is a problem that the removal cannot be achieved by buoyancy.

As other methods for removing the bubble attached to the detection part, a method for increasing the buoyancy applied to the air bubble to remove the air bubble by decompressing inside of the flow path to enlarge a size of the air bubble or a method for stirring liquid in the vicinity of the detection part by using a stirring device such as a stirrer in the flow path may be employed.

However, in the case of the former, since a pump for decompressing inside of the flow path is separately required, and accordingly, a device configuration becomes not only complicated, but also cost is increased. Thus, this method is not preferable. Additionally, in the case of the latter, since it is required to contain the stirrer in the flow path, the configuration becomes not only complicated, but also requires an external force to drive the stirrer. Thus, there is a problem that the device configuration becomes further complicated.

SUMMARY OF THE INVENTION

Technical Problem

The present invention aims to address the above problems, and has as a main objective of, with a simple configuration, removing an air bubble attaching to a detection part arranged in a stepwise concave portion on a wall surface in a flow path, or an air bubble generated in the vicinity, without requiring an external driving force.

Solution to Problem

Accordingly, a liquid sample analyzer according to the present invention includes: a liquid sample flow path for circulating a liquid sample; a detection part contained and arranged in a stepwise concave portion, formed on an inner wall surface of the liquid sample flow path; and a projection part provided at a position facing to the stepwise concave portion on an inner wall surface of the liquid sample flow path, the projection part generating a turbulent flow on a front side of an opening of the stepwise concave portion, wherein the projection part is formed so that a downstream side edge at the top part can be positioned on the front side of the opening of the stepwise concave portion.

Using the liquid sample analyzer, in the configuration where the detection part is arranged in the stepwise concave portion formed on the inner wall surface of the liquid sample flow path, since the projection part is provided at the front of the opening of the stepwise concave portion to generate the turbulent flow, the liquid sample flows toward the detection part side due to the turbulent flow. Thus, it is possible to remove the air bubbles attached to the detection part and to prevent the air bubbles from being generated in the vicinity of the detection part. In this instance, since turbulence in the flow of the liquid sample is generated after passing the downstream side edge at the top part of the projection part, the air bubble can be removed efficiently due to the turbulent flow when the downstream side edge is positioned on the front side of the opening of the stepwise concave portion. In addition, the flow path is narrowed by the projection part to increase a flow velocity of the liquid sample, and accordingly, it becomes possible to make attachment of the air bubbles difficult and to create greater turbulent flow in the lower stream than over the projection part, which allows the sample liquid to easily flow toward the detection part side. Therefore, due to the flow of the liquid sample, it is possible to remove the air bubbles attaching to the detection part and to prevent the air bubbles from being generated in the vicinity of the detection part. As such, it is possible to prevent: undesired fluctuations in an amount of a signal from the detection part; and, insulation of the detection part due to the attachment of air bubbles, and accordingly, the accuracy of a measurement may be prevented from deteriorating due to the air bubbles.

In addition, in order to efficiently flow the liquid sample toward the detection part side while the turbulent flow is generated by the projection part, it is desired that the projection part is formed on a wall surface facing the stepwise concave portion in the inner wall surface of the liquid sample flow path.

In one particular configuration of the liquid sample analyzer, in which the problems of the present invention become pronounced, it is desired to include: a base material forming a concave groove on the surface; and a film adhered to a surface of the base material by an adhesive sheet, the film blocking the concave groove together with the adhesive sheet to form the liquid sample flow path, wherein the detection part is arranged on an adhesive surface of the film, and the stepwise concave portion is formed by the adhesive sheet and the adhesive surface of the film.

Advantageous Effects of Invention

According to the present invention, configured as described, an air bubble attaching to a detection part arranged in a stepwise concave portion on a wall surface in the flow path or an air bubble generated in the vicinity of the detection part may be removed from a cartridge with a simple configuration without requiring an external driving force.

BRIEF DESCRIPTION OF DRAWINGS

FIG. 1 is an overall schematic diagram schematically illustrating a configuration of a cell count measuring instrument according to the present embodiment.

DETAILED DESCRIPTION OF THE EMBODIMENTS

One embodiment of a cell count measuring instrument serving as a measurement instrument according to the present invention will hereinafter be described with reference to the drawings.

Figure 2:
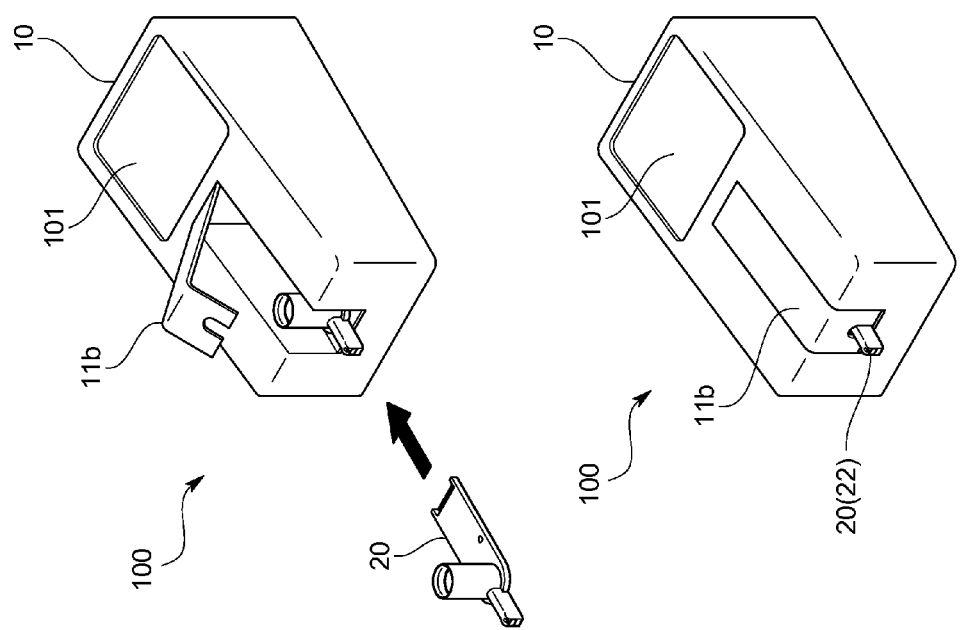
FIG. 2 is a perspective view schematically illustrating cartridge attachment in the cell count measuring instrument according to the same embodiment.

A cell count measuring instrument 100 according to the present embodiment is provided with, as illustrated in FIGS. 1 and 2, a measurement main body 10, and a cartridge 20 that is a liquid sample analyzing device detachably attached to the measurement main body 10. The measurement main body 10 is provided with: an attachment part 11 that is attached with the cartridge 20; a drive part 12 that slides a slide body 202 (to be described later) provided in the cartridge 20; a liquid supply part 13 for circulating diluted sample blood (hereinafter simply referred to as diluted blood), which serves as liquid to be measured, inside the cartridge 20; a connector part 14 for extracting a signal from the cartridge 20; and a calculation part 15 that detects the electrical signal from the connecter part 14 to calculate a cell count contained in the liquid to be measured.

The attachment part 11 is formed to be slightly larger than a width and thickness of a fore end corresponding to an insertion side end part of the cartridge 20, and is provided with a groove-like concave portion 11a (see FIG. 1) that is configured to have a predetermined depth so as to meet a shape of the insertion side end part of the cartridge 20, and a cover body 11b (see FIG. 2) that, when the cartridge 20 is inserted into the concave portion 11a, covers most of the cartridge 20 except a part (including a blood quantity determination part 22) for gripping the cartridge 20. Also, in a deep part of the concave portion 11a, a projection part 16 is formed that is to fit into a cutout part 21 (see FIGS. 3 and 4, and other drawings) formed in the fore end of the cartridge 20, and on a surface of the projection part 16, there is formed a part (conduction part 14a) of the connector part 14 that comes into contact with electrodes 28, 29, and 221 provided in the cartridge 20 to receive the electrical signal.

The drive part 12 is configured to use an engaging pawl to engage with a locking part 202a (specifically, a locking hole, see FIG. 4) provided in the slide body 202 of the cartridge 20, and a slide moving mechanism using a rack-and-pinion mechanism, motor, and the like that moves the engaging pawl in a slide direction (both not illustrated). Also, the drive part 12 is configured such that, in order to quantify blood, the slide body 202 slides between a blood quantity determination position X (see FIG. 5) and a blood introduction position Y (see FIG. 6) for mixing quantified blood with a reagent to introduce them into a mixing flow path 25 and a measuring flow path 26.

The liquid supply part 13 primarily includes a suction pump and a valve. The suction pump is configured such that, when the cartridge 20 is attached to the attachment part 11 and connected to an end point opening part H of the measuring flow path 26 (to be described later), the liquid supply part 13 depressurizes the opening part H, and provides suction to introduce the quantified blood and reagent into the mixing flow path 25 and measuring flow path 26 from a flow path inlet 24.

The connector part 14 is provided with the conduction part 14a that is electrically conducted to an inside of the concave portion 11a of the attachment part 11, such that, when the cartridge is attached, the connector part 14 comes into contact with the electrode 28 of the cartridge 20 to apply a predetermined voltage to the electrode 28, and detects, as the electrical signal, a current amount proportional to an electrical resistance generated at the time of the application. Then, the connector part 14 outputs the electrical signal to the calculation part 15 through a wiring line, such as a lead.

The calculation part 15 is provided with an electrical circuit (not illustrated) that converts the electrical signal outputted from the connector part 14 to a pulse signal to output it as a blood cell count and blood cell volume value of the diluted blood introduced into the measuring flow path 26. Then, the signal regarding the blood cell count and blood cell volume outputted in the above manner is outputted to a display 101, or the like.

Next, a detailed configuration of the cartridge 20 is described with reference to FIGS. 3 to 10.

Figure 3:
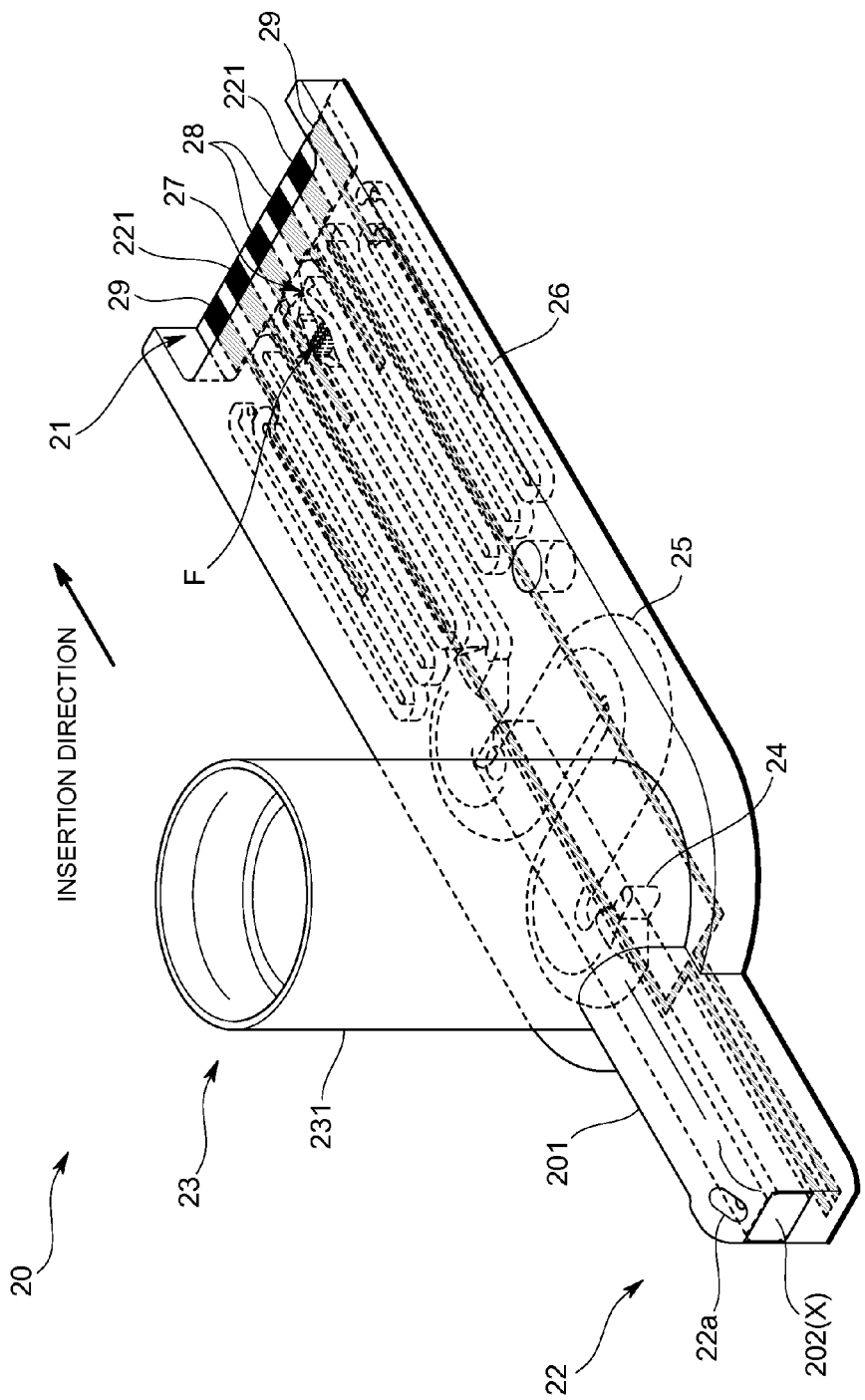
FIG. 3 is a perspective view of a cartridge according to the same embodiment.
Figure 4:
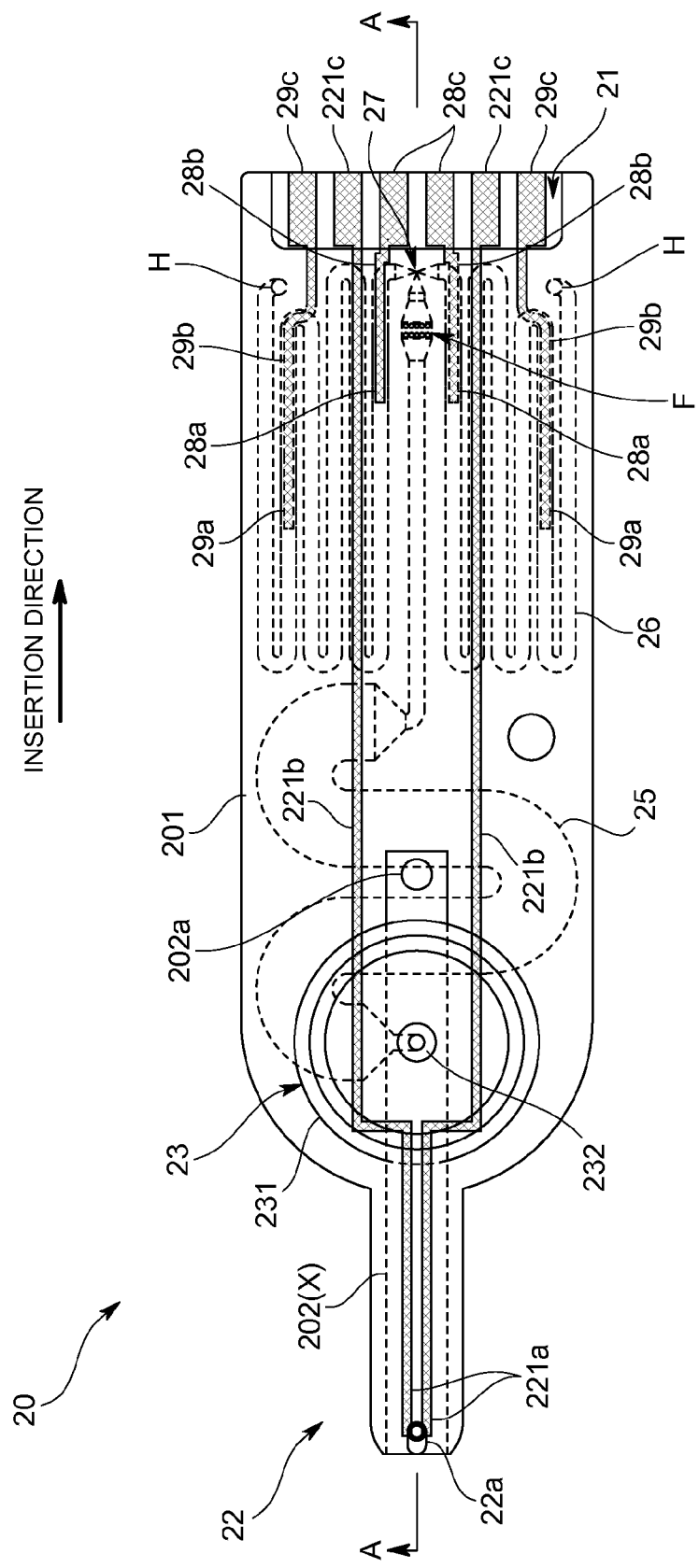
FIG. 4 is a plan view of the cartridge according to the same embodiment.

As illustrated in FIGS. 3 and 4, the cartridge 20 is essentially a one-time-use disposable cartridge, and is provided with the cutout part 21 having a substantially rectangular cross-sectional shape on the fore end side in an insertion direction thereof, and substantially near the center of an end part on a side opposite to the fore end side in the insertion direction, the blood quantity determination part 22 having a blood inlet 22a that is opened on a surface of the blood quantity determination part 22. Also, the cartridge 20 is provided with a reagent container attachment part 23 that is attached with a reagent container 3 for diluting blood quantified by the blood quantity determination part 22, a flow path inlet 24 that introduces the quantified blood and reagent, a mixing flow path 25 that is formed with and is communicatively connected to the flow path inlet 24, and a measuring flow path 26 for calculating the blood count contained in the diluted blood that is formed by the mixing through the mixing flow path 25.

Figure 5:
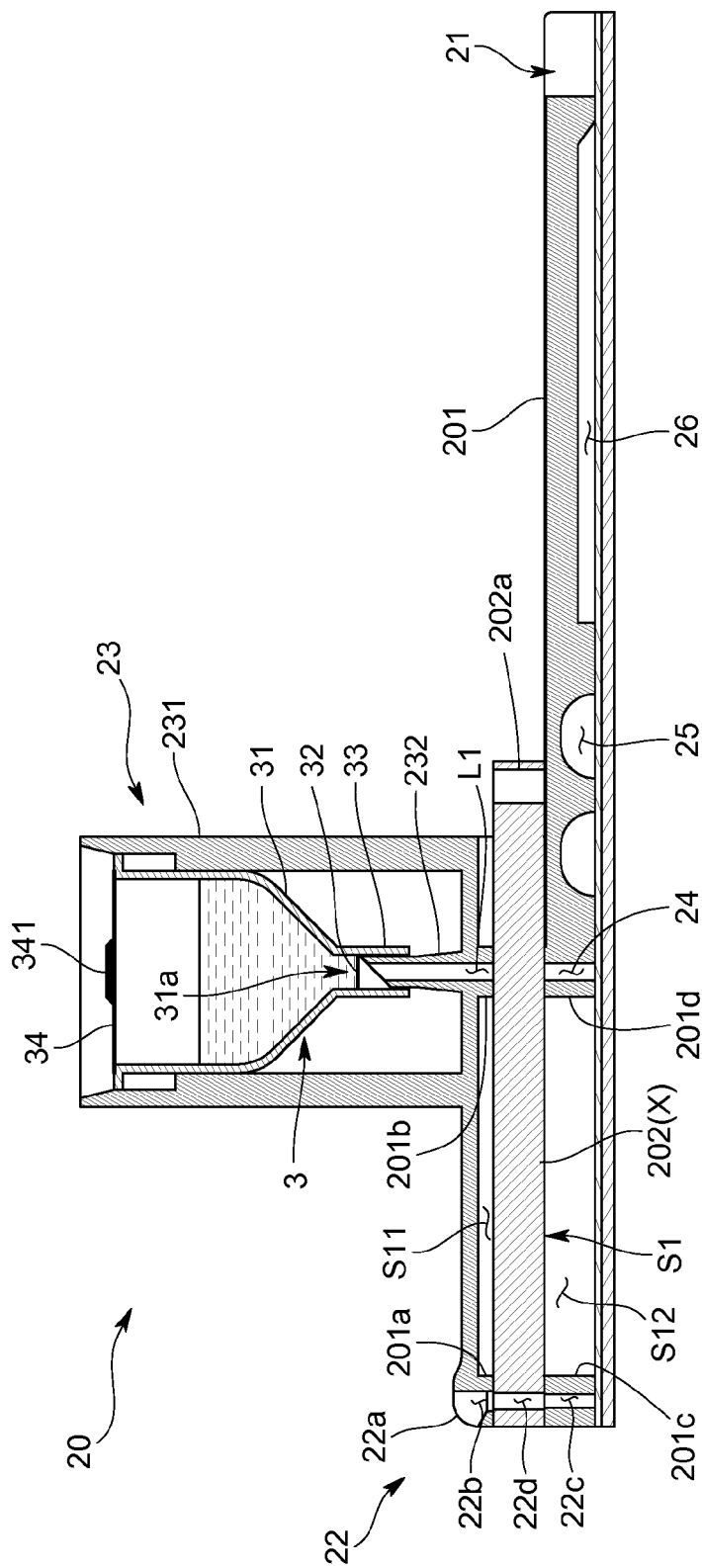
FIG. 5 is an A-A line cross-sectional view of the cartridge at a blood quantity determination position.
Figure 6:
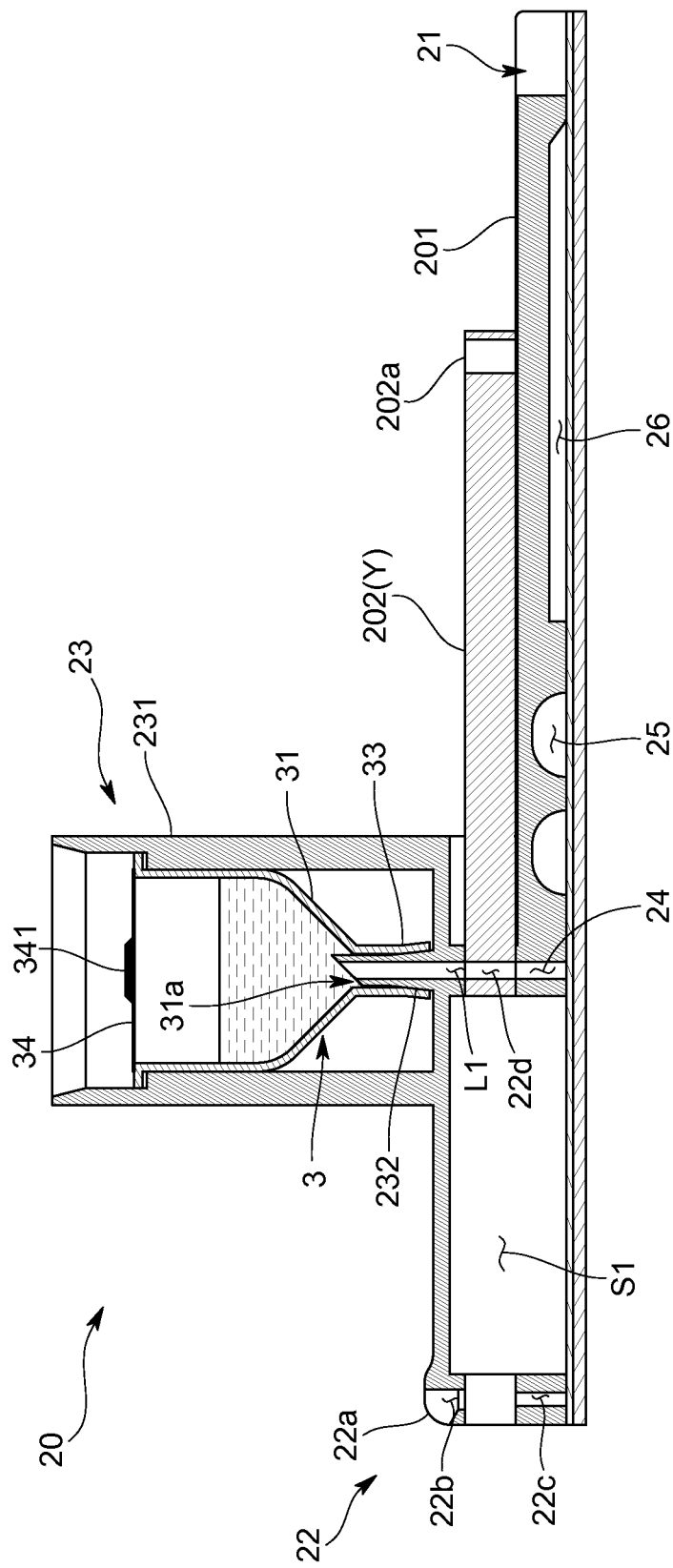
FIG. 6 is an A-A line cross-sectional view of the cartridge at a blood introduction position.

As illustrated in FIGS. 5 and 6, the blood quantity determination part 22 includes: a cartridge main body 201 having an upstream side capillary flow path 22b that is formed in series with the blood inlet 22a and a downstream side capillary flow path 22c, both of which sandwich a space S1 (space forming a slide path for the after-mentioned slide body 202), along with the upstream side capillary flow path 22b; and the slide body 202 that is slidably provided in the space S1, communicatively connects the upstream side capillary flow path 22b and the downstream side capillary flow path 22c to each other, and is formed with a quantity determining capillary flow path 22d, which quantifies blood introduced from the blood inlet 22a and has a predetermined flow path volume.

In this configuration, the engaging pawl of the drive part 12 engages with the locking part 202a formed on the insertion direction side. Via the drive part 12, the slide body 202 slides between the blood quantity determination position X (FIG. 5), wherein the quantity determining capillary flow path 22d is communicatively connected to the upstream side capillary flow path 22b and the downstream side capillary flow path 22c, and the blood introduction position Y (FIG. 6), for introducing the blood quantified by the quantity determining capillary flow path 22d and the reagent into the flow path inlet 24.

Figure 7:
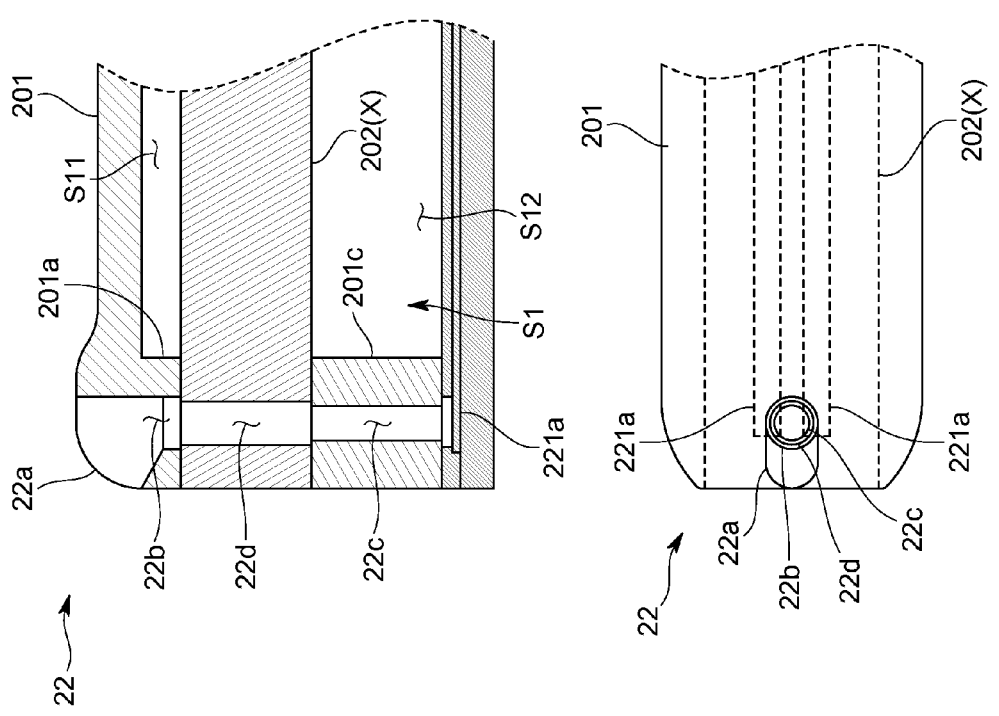
FIG. 7 is a partially enlarged cross-sectional view and a partially enlarged plan view of a blood quantity determination part according to the same embodiment.

In particular, as illustrated in an upper diagram of FIG. 7, the upstream side capillary flow path 22b, the downstream side capillary flow path 22c, and the quantity determining capillary flow path 22d are linear flow paths, respectively having constant cross-sectional circular shapes, and formed so as to face in the same direction (in the present embodiment, a vertical direction orthogonal to the insertion direction). Also, the upstream side capillary flow path 22b, quantity determining capillary flow path 22d, and downstream side capillary flow path 22c are successively reduced in diameter, in this order. That is, the quantity determining capillary flow path 22d is configured to be smaller in diameter than the upstream side capillary flow path 22b, and the downstream side capillary flow path 22c is configured to be smaller in diameter than the quantity determining capillary flow path 22d. This enables capillary forces to be enhanced toward the downstream side, and blood to be surely introduced into the quantity determining capillary flow path 22d. In addition, the upstream side of the upstream side capillary flow path 22b is of a funnel shape that increases in diameter toward the upstream side, and the blood inlet 22a, corresponding to an opening on the upstream side of the funnel shape, is configured to be a long-hole shape, and formed in a corner part of the cartridge main body 201 to open on upper and side surfaces of the cartridge main body 201. This makes it easy to introduce blood from the blood inlet 22a.

Also, as illustrated in a lower diagram of FIG. 7, the upstream side capillary flow path 22b and the downstream side capillary flow path 22c are formed concentrically in a plan view, and a downstream side opening of the upstream side capillary flow path 22b is opened to the space S1 (slide path), and an upstream side opening of the downstream side capillary flow path 22c is opened to the space S1 (slide path).

Further, when the slide body 202 is at the blood quantity determination position X, in the plan view, an upstream side opening of the quantity determining capillary flow path 22d is contained in the downstream side opening of the upstream side capillary flow path 22b, and the upstream side opening of the downstream side capillary flow path 22c is contained in a downstream side opening of the quantity determining capillary flow path 22d. In the present embodiment, when the slide body 202 is at the blood quantity determination position X, the quantity determining capillary flow path 22d is positioned concentrically with respect to the upstream side capillary flow path 22b and the downstream side capillary flow path 22c.

Note that, in order to detect that the quantity determining capillary flow path 22d is filled with blood, as illustrated in FIGS. 4 and 7, on a downstream side of the downstream side capillary flow path 22c, a liquid sensor 221 for detecting whether or not blood has reached the downstream side capillary flow path 22c, is provided. The liquid sensor 221 is configured to have electrodes, and includes: a liquid contacting part 221a that is provided so as to block all or a part of a downstream side opening of the downstream side capillary flow path 22c; a lead 221b that is drawn from the liquid contacting part 221a; and a signal extraction part 221c, which is exposed on a cartridge surface below the cutout part 21 so as to be electrically conducted to the liquid contacting part 221a through the lead 221b.

In the slide path S1, into which the slide body 202 is slidably inserted, there is formed a blood reduction preventing structure that, in the process of sliding the slide body 202 between the blood quantity determination position X and the blood introduction position Y, prevents a phenomenon in which an inner wall surface of the slide path S1 comes into contact with the upper and lower openings of the quantity determining capillary flow path 22d and quantified blood adheres to the inner wall surface, and is thereby reduced in quantity.

The blood reduction preventing structure, as illustrated in FIGS. 5 and 6, and other drawings, is provided with: an upper gap S11 that is provided between a forming wall part 201a, forming the upstream side capillary flow path 22b, and a forming wall part 201b, forming a reagent introduction path L1; and a lower gap S12 that is provided between a forming wall part 201c, forming the downstream side capillary flow path 22c, and a forming wall part 201d, forming the flow path inlet 24. Because of the configuration of the upper gap S11, the upstream side opening of the quantity determining capillary flow path 22d is configured to not come into contact with an upper wall surface of the cartridge main body 201. Similarly, because of the configuration of the lower gap S12, the downstream side opening of the quantity determining capillary flow path 22d is configured not to come into contact with a lower wall surface of the cartridge main body 201.

Also, by employing such a configuration, as illustrated in the upper diagram of FIG. 7, even if in the state where the slide body 202 is at the blood quantity determination position X, and blood introduced from the blood inlet 22a intrudes into a gap between the cartridge main body 201 and the slide body 202 (gap between the slide path S1 and the slide body 202), the intruding blood is stopped at end parts of the upper gap S11 and the lower gap S12. Therefore, the blood introduced from the blood inlet 22a can be introduced into the upstream side capillary flow path 22b, the quantity determining capillary flow path 22d, and the downstream side capillary flow path 22c without waste.

The reagent container attachment part 23 is detachably attached with the reagent container 3, serving as a liquid container for analysis, and as illustrated in FIGS. 5 and 6, is provided with: a container storage part 231 that is provided on an upper surface of the cartridge main body 201 and stores the reagent container 3; and a reagent lead-out needle 232 that is provided so as to extend from a bottom wall of the container storage part 231 and passes through a seal part 32 of the reagent container 3 stored in the container storage part 231. The reagent lead-out needle 232 is communicatively connected to the reagent introduction path L1, of which an internal flow path is opened to the space S1.

Note that the reagent container 3 is one that contains the reagent serving as a predetermined quantity of liquid for analysis, and as illustrated in FIG. 5, is provided with: a container main body 31, of which a bottom wall is formed with an opening part 31a that enables the reagent to be led out; a seal part 32 that seals the opening part 31a; and a guide part 33 that is provided outside the seal part 32 and is substantially cylindrically shaped.

The container main body 31 has a shape substantially in the form of a surface of revolution, and the bottom wall is funnel shaped. Also, the opening part 31a is formed in substantially the center of the bottom wall. Further, the guide part 33 is provided so as to cover a circumference of the seal part 32, and serves as a guide for inserting the reagent lead-out needle 232 into the seal part 32. When the reagent lead-out needle 232 is inserted into the seal part 32, the seal part 32 comes into substantially liquid-tight contact with an outer circumferential surface of the reagent lead-out needle 232.

The reagent container 3 of the present embodiment is made of resin such as polypropylene, and the container main body 31, the seal part 32, and the guide part 33 are formed by integral molding. An upper part of the reagent container 3 is opened, and after the reagent has been contained from the opening, sealed by a sealing film 34, such as an aluminum film. The sealing film 34 is provided with an atmospheric opening part 341 including, for example, a resin check valve, and simultaneously with or before the insertion of the reagent lead-out needle 232 into the seal part 32, a ventilation needle (not illustrated) is inserted to open the reagent container 3 to the atmosphere.

The guide part 33 comes into close and substantially liquid-tight contact with the outer circumferential surface of the reagent lead-out needle 232 before the reagent lead-out needle 232 is inserted into the seal part 32. Specifically, the reagent lead-out needle 232 gradually increases in diameter from a fore end toward a base end, and the guide part 33 is configured such that as the reagent lead-out needle 232 is inserted into the guide part 33, a fore end of the guide part 33 deforms as it comes into close contact with and engages with the outer circumferential surface of the reagent lead-out needle 232. Thereby, the guide part 33 comes into liquid-tight contact with the outer circumferential surface of the reagent lead-out needle 232 (see FIG. 6). That is, an inside diameter of the guide part 33 is formed to be slightly smaller than an outside diameter of the base end of the reagent lead-out needle 232. Also, an axial length of the guide part 33 is of a length long enough to, before the reagent lead-out needle 232 is inserted into the seal part 32, bring an inner circumferential surface of the guide part 33 into substantially liquid-tight contact with the whole of the outer circumferential surface of the reagent lead-out needle 232 in a circumferential direction. By providing the guide part 33 in the reagent container 3, as described, the reagent can be prevented from leaking outside the reagent container 3 at the time of or after the insertion.

The mixing flow path 25, as illustrated in FIGS. 3 and 4, is formed in series with the flow path inlet 24 opened to the slide path S1, and is also formed so as to meander in a serpentine manner inside the cartridge main body 201. The sample inlet 24 is, in the state where the slide body 202 is at the blood introduction position Y, communicatively connected to the downstream side opening of the quantity determining capillary flow path 22d (see FIG. 6). In this state, because of the suction by the liquid supply part 13, the reagent is introduced together with blood inside the quantity determining capillary flow path 22d, and into the mixing flow path 25 through the quantity determining capillary flow path 22d from the reagent introduction path L1, communicatively connected to the reagent lead-out needle 232 inserted into the reagent container 3. Then, by the suction/discharge operation of the pump of the liquid supply part 13, the quantified blood and reagent are mixed in the mixing flow path 25 to form diluted blood.

The measuring flow path 26 serving as a liquid sample flow path, as illustrated in FIGS. 3 and 4, is formed so as to be communicatively connected to a downstream side outlet of the mixing flow path 25, and configured to linearly extend from the downstream side outlet toward the fore end side so as to halve the whole of the cartridge main body 201. The measuring flow path 26 is narrowed such that inner walls facing to each other in the flow path 26 form a gap of approximately 1 mm near the cutout part 21 on the fore end side, and via the gap, an aperture part 27 is formed. Note that a size of the gap for forming the aperture part 27 can be appropriately set depending on a size of a cell to be measured (in the present embodiment, a blood cell).

Figure 8:
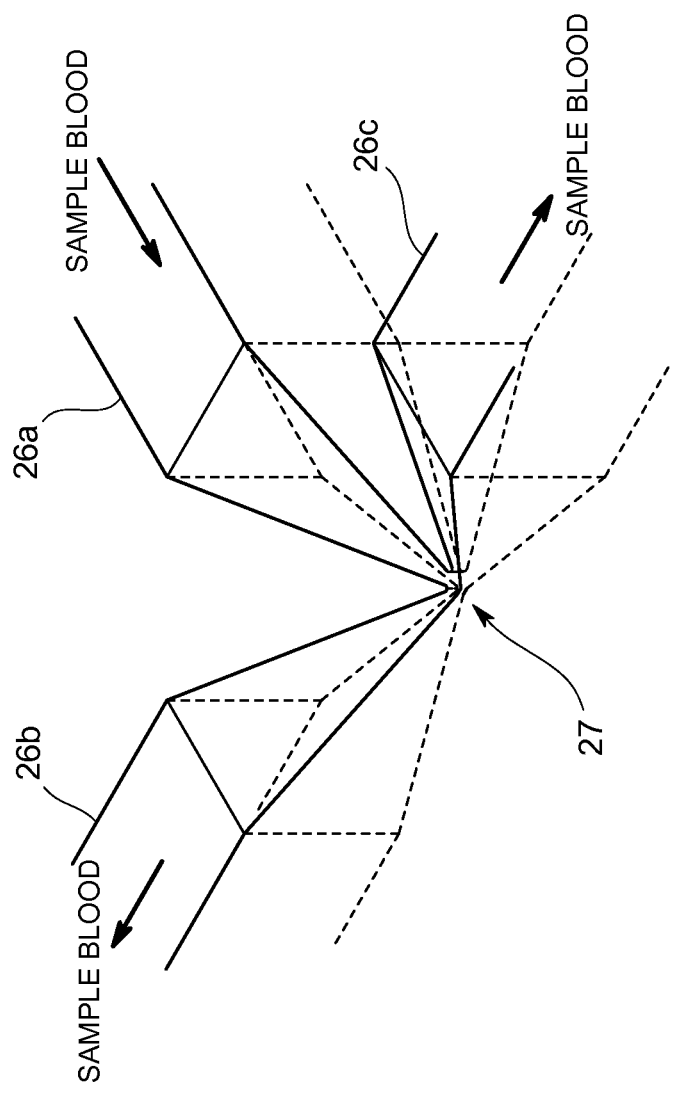
FIG. 8 is an enlarged perspective view illustrating an aperture part according to the same embodiment.

Also, the measuring flow path 26, in particular as illustrated in FIG. 8, is divided into two branches toward the downstream side from the position where the aperture part 27 is formed. Among the measuring flow paths 26 near the aperture part 27, the flow path 26a on the upstream side of the aperture part 27 is configured so as to gradually narrow a distance between the inner walls facing to each other toward the aperture part 27, and each of the flow paths 26b and 26c on the downstream side is configured so as to gradually expand a distance between inner walls facing to each other from the aperture part 27. In other areas, the flow path width is substantially constant. By forming the measuring flow path 26 as described, a flow of the diluted blood passing through the aperture part 27 is not disturbed, and blood cells contained in the diluted blood pass through the aperture part 27 in sequence.

Figure 9:
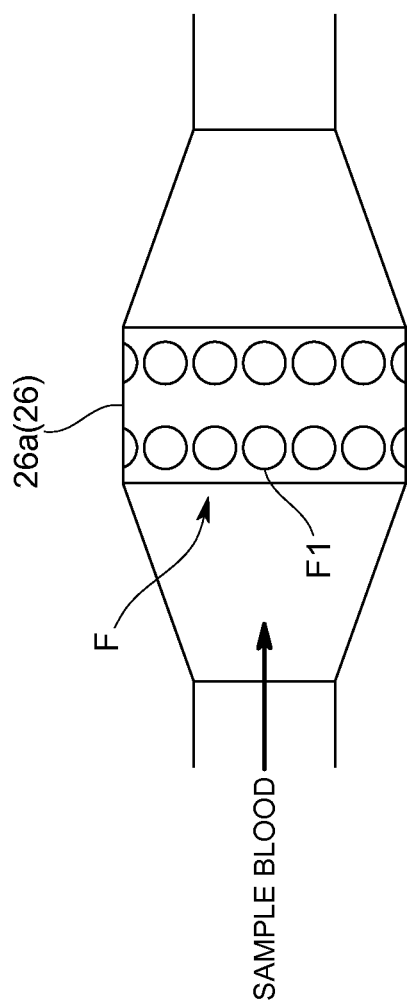
FIG. 9 is a partially enlarged cross-sectional view and a partially enlarged plan view illustrating a filter part according to the same embodiment.

Note that, on the upstream side of the aperture part 27, a filter part F is formed. The filter part F is, as illustrated in FIG. 9, formed of a plurality of columnar parts F1 that are respectively arranged at predetermined intervals. The columnar parts F1 are regularly arranged at the intervals that enable the blood cells, such as red blood cells, white blood cells, and platelets, to pass through. For example, each of the columnar parts F1 is of a cylindrical shape having a diameter of 0.3 mm, and in a direction in which the columnar parts F1 block the flow path (in a direction orthogonal to the flow path direction), the columnar parts F1 are linearly arranged at the intervals of, for example, 30 to 60 μm, and preferably 50 μm. In the present embodiment, the columnar parts F1 are arranged in two lines to form the filter part F, enabling the red blood cells (cell diameter of approximately 8 μm), white blood cells (cell diameter of approximately 10 to 20 μm), platelets (cell diameter of approximately 2 to 3 μm) and the like to pass through the filter part F, and stopping foreign substances such as dust and dirt, each having a diameter of 50 μm or more, at the filter part F. This prevents the foreign substances from reaching the electrodes 28 and 29, and therefore measurement accuracy of the blood analysis can be improved.

Turning now to describe the flow paths 26b and 26c on the downstream side of the aperture part 27, each of the flow paths 26b and 26c is formed to be slightly linear from the branch position along a fore end side of the cartridge main body 201, then bends and linearly extends toward a rear end of the cartridge, and again extends from the rear end to the fore end. By repeating this multiple times, each of the flow paths 26b and 26c is formed in a zigzag pattern (see FIG. 4). As described, the measuring flow path 26 is configured to bend multiple times at the end part side with respect to the insertion direction of the cartridge main body 201, and formed over substantially the whole area of the cartridge main body 201. This enables the measuring flow path 26 to be as long as possible within a limited area inside the cartridge main body 201. Also, the measuring flow path 26 is configured such that final end parts thereof are communicatively connected to opening parts H, opened on a surface (lower surface) of the cartridge main body 201, and the diluted blood introduced from the flow path inlet 24 travels in the measuring flow path 26 so as to push out air contained in the measuring flow path 26 from the opening parts H.

Also, as illustrated in FIG. 4, in positions on the downstream side of the aperture part 27 at the branch position of the measuring flow path 26, which are in contact with the diluted blood having passed through the aperture part 27, the pair of electrodes 28 (hereinafter also referred to as first electrodes 28) are arranged so as to sandwich the aperture part 27. Each of the first electrodes 28 includes: a liquid contacting part 28a that is formed so as to face to the inner wall of the measuring flow path 26; a lead 28b that is drawn from the liquid contacting part 28a; and a signal extraction part 28c that is exposed on the cartridge surface on the cutout part 21 so as to be electrically conducted to the liquid contacting part 28a through the lead 28b.

Also, on a downstream side of the liquid contacting part 28a in the first electrode 28, the second electrode 29 is provided. The second electrode 29 includes: a liquid detection part 29a, which is provided on a downstream side where a flow path volume from the liquid contacting part 28a becomes equal to a predetermined constant volume (specifically, on an upstream side from the end point of the measuring flow path 26 by a predetermined distance); a lead 29b that is drawn from the liquid detection part 29a; and a detected signal output part 29c that is in series with an end point of the lead 29b and is provided laterally to the signal extraction part 28c, and acts as a liquid level sensor adapted to detect that the diluted blood has reached the liquid detection part 29a.

Accordingly, when the diluted blood traveling in the measuring flow path 26, after coming into contact with the liquid contacting part 28a, comes into contact with the liquid detection part 29a, an electrical signal is generated, and the electrical signal is sent to the detected signal output part 29c through the lead 29b drawn from the liquid detection part 29a, which informs the measurement main body 10 that the diluted blood has reached a predetermined reaching position in the measuring flow path 26. As described, when it is detected that the diluted blood has reached the predetermined position in the measuring flow path 26, the liquid supply part 13 stops supplying the diluted blood, and thereby the diluted blood can be prevented from reaching the opening part H at the end point of the flow path and overflowing.

Note that the signal extraction part 28c of the first electrode 28 and the detected signal output part 29c of the second electrode 29 are, as described above, arranged side by side, and configured to, when the cartridge 20 is attached to the measurement main body 10, come into electrical contact with the conduction part 14a of the connector part 14.

Figure 10:
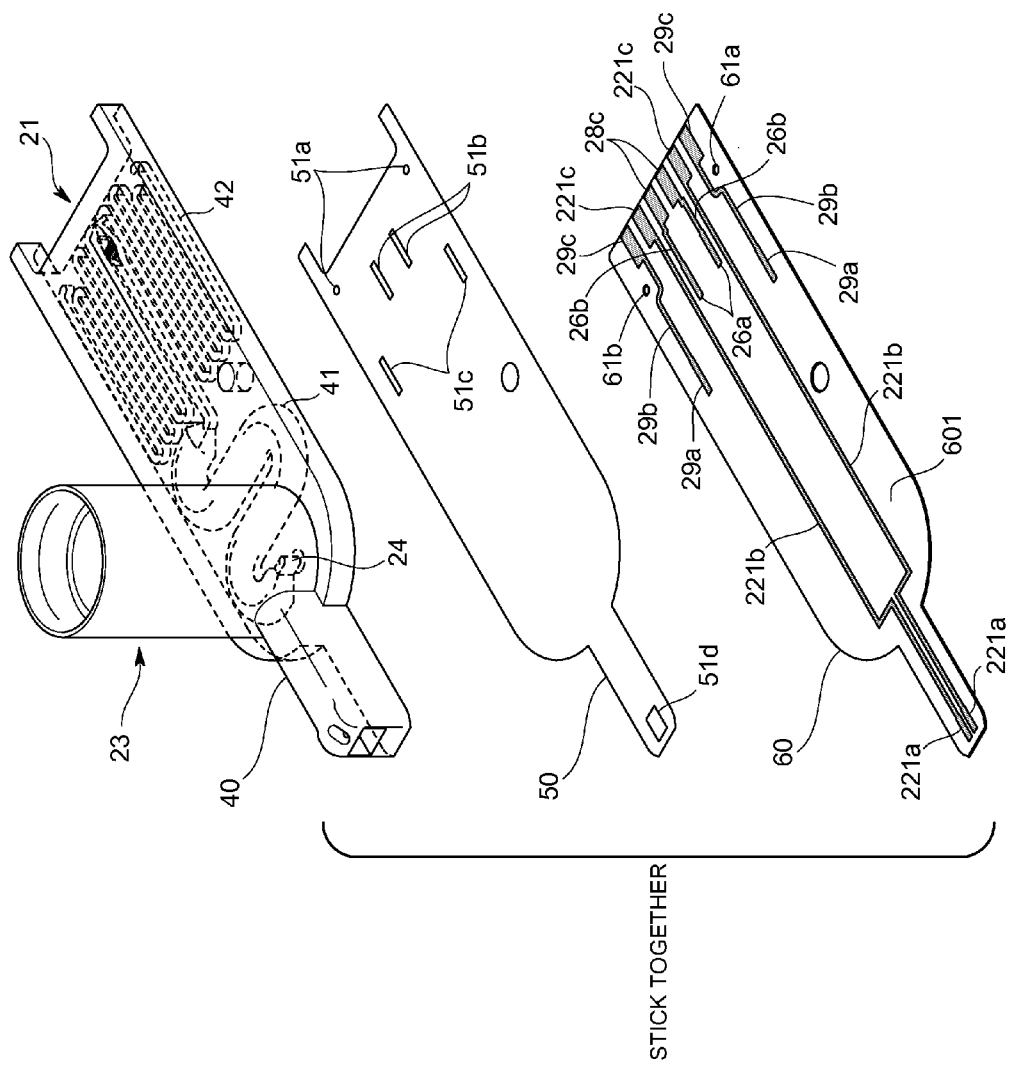
FIG. 10 is a perspective view illustrating a situation in which a cartridge main body according to the same embodiment is decomposed on a main component basis.

Next, details of an internal configuration of the cartridge main body 201 are described with reference to FIG. 10. The cartridge main body 201 includes, as illustrated in FIG. 10, a base material 40 that has a surface formed with bottom-equipped grooves 41 and 42 and is made of, for example, PMMA, and a film 60 that is adhered to the surface (lower surface) of the base material 40 via an adhesive sheet 50 and serves as a covering member made of PET.

Substantially near the center on a fore end side of the base material 40, a concave portion forming the cutout part 21 of the cartridge main body 201 is formed, and also the first bottom-equipped groove 41, forming the mixing flow path 25, and the second bottom-equipped groove 42, forming the measuring flow path 26, are formed. The first bottom-equipped groove 41 is a semicircular groove that is opened on the base material surface (lower surface) and has a width of approximately 4 mm and a depth of approximately 2 mm, and the second bottom-equipped groove 42 is a concave groove that is opened on the base material surface (lower surface) and has a width of approximately 1 mm and a depth of approximately 1 mm. Also, a start point of the first bottom-equipped groove 41 is provided by the flow path inlet 24. Corresponding to the flow path inlet 24 and through the space S1 formed inside the base material, the sample introduction path L1 and the reagent container attachment part 23 are formed respectively inside the base material and on a base material surface (upper surface on a side opposite to the surface formed with the grooves). Also, a start point of the second bottom-equipped groove 42 is in series with an end point of the first bottom-equipped groove 41. Further, as described above, near the upstream side of the position where the aperture part 27 is formed, the width of the second bottom-equipped groove 42 is gradually narrowed, and near the downstream side of the position where the aperture part 27 is formed, the width of the second bottom-equipped groove is gradually expanded. As such, bottom-equipped groove 42 and columnar parts F1 of the filter part F may be formed by any fabrication method such as micromachining fabrication, hot emboss fabrication, or optical molding, or in the case of forming the base material 40 with resin, by a method such as precision injection molding. Molding may be performed so as to form a shape preliminarily having such grooves.

Also, the film 60 is formed to have a shape that substantially coincides with the shape of the base material surface, and when adhered to the base material surface, covers opening parts of the bottom-equipped grooves 41 and 42 to thereby form the mixing flow path 25 and the measuring flow path 26, and at the positions corresponding to end points of the second bottom equipped groove 42, through-holes 61a and 61b are formed. Also, the film 60 is not provided with a cutout in a position corresponding to the cutout part 21 of the base material 40, and is configured such that when the base material 40 and the film 60 are bonded to each other, a part of the film 60 covers an upper-side of the cutout part 21. In addition, in an area covering the upper-side of the cutout part 21, the signal extraction part 28c, which is a part of the first electrode 28, the detected signal output part 29c, which is a part of the second electrode 29, and the signal extraction part 221c, which is a part of the liquid sensor 221, are formed.

Also, by applying a thin carbon coat (C) on a small amount of silver (Ag) that is coated in predetermined positions on a surface 601 of the film 60 and serves as conductive metal, the above-described first and second electrodes 28 and 29 are formed. As described above, the liquid contacting part 28a and the liquid detection part 29a, respectively constituting the electrodes, come into contact with the diluted blood flowing through the measuring flow path 26 to be thereby electrically conducted to each other, and are also electrically connected to the signal extraction part 28c and the detected signal output part 29c through the leads 28b and 29b, respectively. In addition, the liquid sensor 221 may be formed in the same manner.

Also, the first and second electrodes 28 and 29, formed on the surface 601 of the film 60, are formed by a method such as screen printing or sputtering. It should be appreciated that these electrodes can also be formed by a method other than the above-described ones, and even in a case of using a method that deposits a layer of a mixed material of silver and carbon on the whole of a back surface of the film 60, and removes or metamorphoses silver in unnecessary parts by etching or electrical treatment, these electrodes can be formed. In this case, as compared with the above-described electrodes formed by the screen printing or sputtering, the electrodes having a smaller film thickness can be formed. In addition, the liquid sensor 221 is formed in the same manner.

Also, the adhesive sheet 50 for bonding the base material 40 and the film 60 to each other is formed of a thin film-like solid adhesive that covers the whole of the surface of the base material 40, except for parts corresponding to the locations where the through-holes 61a and 61b, the liquid contacting parts 28a, the liquid detection parts 29a, and the liquid contacting parts 221a of the film 60 are formed. In FIG. 10, a reference numeral 51a represents through-holes corresponding to the through-holes 61a and 61b, 51b represents rectangular-shaped holes corresponding to the liquid contacting parts 28a, 51c represents rectangular-shaped holes corresponding to the liquid detection parts 29a, and 51d represents a rectangular-shaped hole corresponding to the liquid contacting parts 221a. The adhesive sheet 50 is solid at room temperature; however, it has a property in which when it is heated to a predetermined temperature or more, it melts to give rise to an adhesive property. By sandwiching the adhesive sheet 50 between the base material 40 and the film 60, and heating them in this state, the base material 40 and the film 60 are adapted to be bonded to each other.

Figure 11:
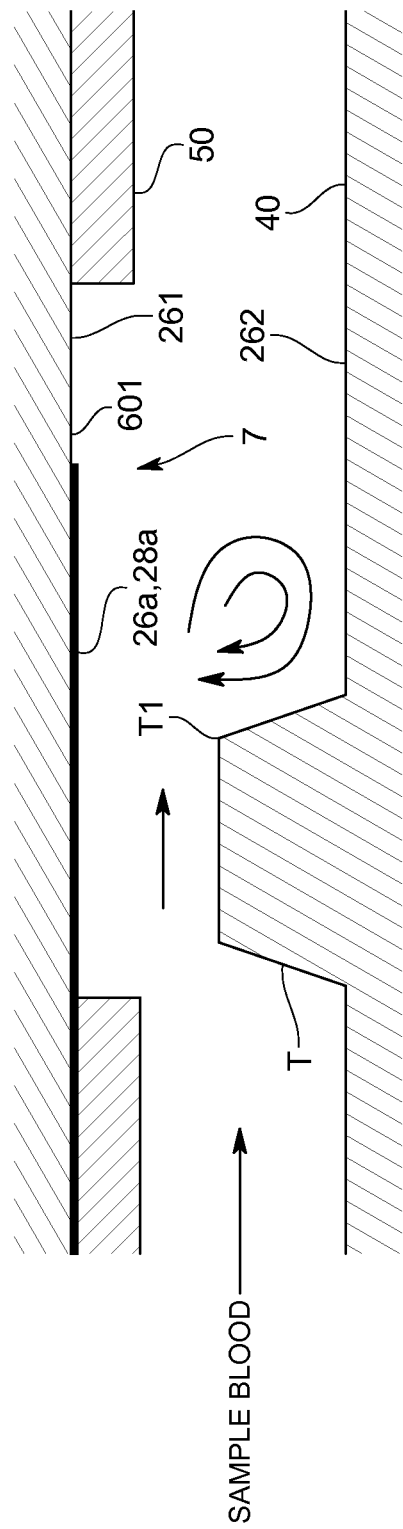
FIG. 11 is a schematic cross-sectional view illustrating the proximity of a detection part of a measuring flow path according to the same embodiment.
Figure 12:
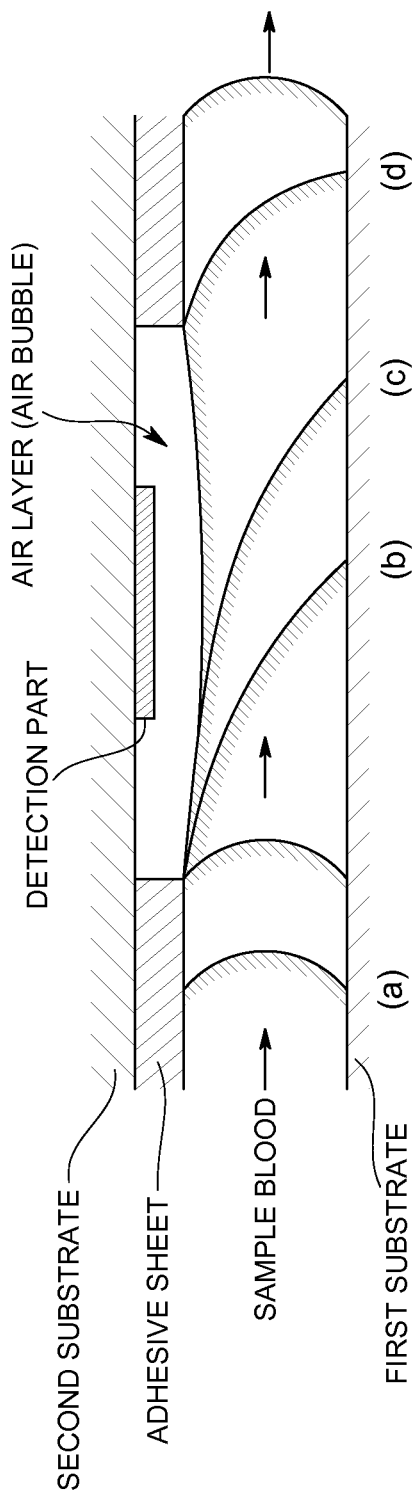
FIG. 12 is a diagram schematically illustrating a flow of a sample blood in a conventional liquid sample flow path.

In the cartridge main body 201, configured as described, the liquid contacting parts 28a of the first electrodes 28 and the liquid detection parts 29a of the second electrodes that are provided on the surface 601 corresponding to an adhesion surface of the film 60 are, as illustrated in FIG. 11, configured to be contained and arranged in a stepwise concave portion 7 formed by the adhesive sheet 50 and the adhesion surface 601 of the film 60. In the present embodiment, thicknesses of the electrodes (liquid contacting parts 28a and liquid detection parts 29a) formed on the surface 601 of the film 60 are approximately 0.015 mm, and a thickness of the adhesive sheet 50 is approximately 0.1 mm, so that the electrodes (liquid contacting parts 28a and liquid detection parts 29a) are completely contained in the stepwise concave portion 7. Note that FIG. 11 illustrates an upside-down diagram.

Also, near the liquid contacting part 28a and the liquid detection part 29a in the measuring flow path 26 having substantially a rectangular cross-sectional shape of the cartridge main body 201, a projection part T is provided at a position facing to the stepwise concave portion 7.

The projection part T is one that generates a turbulent flow in the flow of the diluted blood when the diluted blood circulates on a front side of the opening of the stepwise concave portion 7. Specifically, the projection part T is formed on an inner wall surface 262 (in FIG. 11, lower surface) facing to an inner wall surface 261 (in FIG. 11, upper surface) formed with the stepwise concave portion 7 in the measuring flow path 26, and provided so as to face to the liquid contacting part 28a of the first electrode 28 and the liquid detection part 29a of the second electrode 29. The projection part T is formed over the whole area in a flow path width direction, and has a constant cross-sectional shape in the flow path width direction. That is, the projection part T is formed on a bottom surface of the bottom-equipped groove 42 of the base material 50 in the width direction. The projection part T of the present embodiment is one of which a cross-section along the flow path direction is substantially trapezoidally shaped. Also, at least a downstream side edge T1 of a top surface of the projection part T is positioned on the front side of the opening of the stepwise concave portion 7, i.e., positioned within a flow path range the stepwise concave portion 7 faces to. A position of an upstream side edge of the top surface of the projection part T is not particularly limited; however, the present embodiment illustrates the case where the upstream side edge is positioned near a downside of an upstream side end of the stepwise concave portion 7.

<Measuring Procedure>

Next, a procedure to use such a cell count measuring instrument 100 to measure a blood cell count and a blood cell size in the diluted blood serving as the liquid to be measured is described below.

First, the reagent container 3 is stored in the reagent container attachment part 23 of the cartridge main body 201. At this time, the reagent lead-out needle 232 of the reagent container attachment part 23 is not yet inserted into the seal part 32. Also, a position of the slide body 202 with respect to the cartridge main body 201 corresponds to the blood quantity determination position X. In this state, the cartridge 20 is attached to the measurement main body 10. If the cover body 11b is closed in this state, the ventilation needle provided for the cover body 11b is inserted into the atmospheric opening part 341 of the reagent container 3, and at the same time, the reagent container 3 is attached to the reagent container attachment part 23. That is, the reagent lead-out needle 232 is inserted into the seal part 32. In addition, at this time, the signal extraction parts 28c, detected signal output parts 29c, and signal extraction parts 221c formed on the surface of the cartridge main body 201 come into contact with the conduction part 14a of the connector part 14 to supply a small amount of a current so as to apply a predetermined voltage from the conduction part 14a to the liquid sensor 221, and first and second electrodes 28 and 29 of the cartridge main body 201.

Then, blood is attached to the blood inlet 22a of the cartridge main body 201, which is exposed outside the measurement main body 10. By doing so, the blood attached on the basis of capillary action by the upstream side capillary flow path 22b, quantity determining capillary flow path 22d, and downstream side capillary flow path 22c is introduced inside. At this time, the measurement main body 10 obtains a detected signal from the liquid sensor 221 provided at the downstream side opening of the downstream side capillary flow path 22c to determine whether or not the blood has reached the downstream side capillary flow path 22c. If the measurement main body 10 determines that the blood has reached the downstream side capillary flow path 22c, the measurement main body 10 slides the slide body 202 from the blood quantity determination position X to the blood introduction position Y. At this time, blood outside the quantity determining capillary flow path 22d is struck by the forming wall part forming the upstream side capillary flow path 22b and the forming wall part forming the downstream side capillary flow path 22c, and only the blood retained in the quantity determining capillary flow path 22d moves to the blood introduction position Y.

After the slide body 202 has been moved to the blood introduction position Y, the liquid supply part 13 operates to depressurize the flow path inlet 24, and thereby the blood inside the quantity determining capillary flow path 22d and the reagent are sucked into the mixing flow path 25. Then, the liquid supply part 13 performs the suction/discharge operation of the pump to thereby mix the blood and the reagent in the mixing flow path 25 and/or the reagent container 3. After the mixing, by the liquid supply part 13, the diluted blood is sucked into the measuring flow path 26.

When the diluted blood supplied into the measuring flow path 26 passes through the aperture part 27 and is branched, and the branched diluted blood flows respectively reach the pair of liquid contacting parts 28a, the connector part 14 detects an electrical resistance value between the liquid contacting parts 28a as an electrical signal through the signal extraction parts 28c. The electrical signal is a pulse signal proportional to the electrical resistance value that is varied on the basis of a blood cell count and volume (diameter) in the diluted blood passing through the aperture part 27, and the connector part 14 calculates, from the electrical signal, the blood cell count and volume in the diluted blood having passed through the aperture part 27 for a predetermined period of time (for example, a period of time from a time point when the diluted blood reaches the liquid contacting parts 28a of the first electrodes 28 to a time point when it reaches the liquid detection parts 29 of the second electrodes 29), and then outputs a result of the calculation to the display 101, or the like.

Also, when the diluted blood supplied into the measuring flow path 26 passes through the positions where the first electrode liquid contacting parts 28a are provided, and further reaches the positions where the second electrode liquid detection parts 29a are provided, an electrical resistance value between the first electrodes 28 is detected as an electrical signal through the detected signal output parts 29c and 28c. When the electrical signal is detected in the connector part 14, the calculation is stopped, and also a switching valve is operated to switch the opening parts H from the liquid supply part 13 and communicatively connect the opening parts H to the atmosphere. This returns the opening parts H to the atmospheric pressure to stop the suction of the diluted blood.

When the measurement of the blood cell count in the diluted blood is completed, as described, the cartridge 20 is detached from the attachment part 11, and the cartridge 20 containing the diluted blood is discarded according to a predetermined process, such as incineration.

Effects of Present Embodiment

According to the cell count measuring instrument 100 configured in the above-mentioned manner of the present embodiment, in the structure where the electrodes 28a and 29a are arranged in the stepwise concave portion formed on the inner wall surface of the measuring flow path 26, which is the liquid sample flow path, since the projection part T is provided at a front of the opening of the stepwise concave portion to generate the turbulent flow, the diluted blood flows toward the electrodes 28a and 29a side due to the turbulent flow, and thus it is possible to remove the air bubbles attached to the electrodes 28a and 29a and to prevent the air bubbles from being generated in the vicinity of the electrodes 28a and 29a.

In addition, the measuring flow path 26 is narrowed by the projection part T, and thus the flow velocity of diluted blood is increased. Accordingly, it becomes possible to make the attachment of the air bubbles difficult and to enhance the turbulent flow in the lower current than the projection part T, which makes the diluted blood easily flow toward the electrodes 28a and 29a side.

Therefore, it is possible to remove the air bubbles attached to the electrodes 28a and 29a and to prevent the air bubbles from being generated in the vicinity of the electrodes 28a and 29a due to the flow of the diluted blood. Further, it is possible to prevent unevenness of amounts of signals from the electrodes 28a and 29a, and insulation of the electrodes due to the attachment of air bubbles. Accordingly, the measurement accuracy can be prevented from deteriorating due to the air bubbles.

Other Embodiments

Meanwhile, the present invention is not limited to the above-described embodiments.

For example, in the above-described embodiments, the projection part is substantially trapezoidal in shape in a cross-section along the flow path direction; however, in addition, the cross-section may be in a semicircular shape, in a triangular shape, and in a rectangular shape.

Additionally, the projection parts are formed along a direction of the flow path width on the inner wall surface facing the electrode, and the cross section along the flow path direction is shaped so as to have a uniform section; however, the projection parts may be partially formed on the inner wall surface facing the electrode and may be not shaped so as to have a uniform cross section.

Moreover, the wall surface on which the projection part is provided is not limited to the inner wall surface facing the electrode when arranged at a position facing to the stepwise concave portion in which the electrode is formed, and in a case where the measuring flow path has a cross section substantially formed in a rectangular shape, the projection part may be provided on an inner wall surface perpendicular to the inner wall surface facing the electrode.

In addition, in the blood quantity determination part according to the above-described embodiments, the upstream side capillary flow path, the downstream side capillary flow path, and the quantity determining capillary flow path are linear flow paths shaped so as to have a uniform section, respectively, and additionally, in the flow paths at the blood quantity determination position, when an upstream side opening of the downstream side capillary flow path is included in a downstream side opening of the upstream side capillary flow path and when an upstream side opening of the quantity determining capillary flow path is included in a downstream side opening of the quantity determining capillary flow path, the upstream side capillary flow path, the downstream side capillary flow path, and the quantity determining capillary flow path may be a curved flow path and may be inclined in a perpendicular direction or in a horizontal direction.

Furthermore, in the above-described embodiments, the mixing flow path and the measuring flow path circulate the blood, the reagent, and the diluted blood due to the suction operation of the pump; however, in addition, the flow paths may circulate the blood, the reagent, and the diluted blood due to the capillarity.

Additionally, the above-described embodiments have been explained by exemplifying the blood (diluted blood) as the liquid sample, but can be applied to other liquid sample, such as a body fluid.

Moreover, in the above-described embodiments, the cartridge whose flow path is branched at the aperture part is disclosed; however, the present invention is not limited to the embodiments, and may form the aperture in a general single flow path and arrange the electrodes at an upstream and a downstream sandwiching the aperture part.

In addition, in the above-described embodiments, the timing at which the supply of liquid to be measured into the flow path is stopped is determined in the manner where the second electrode, provided in the flow path, detects the liquid to be measured; however, if a length, and the like, of the flow path formed in the cartridge is designed to be known, a supply amount of the liquid to be measured into the flow path may be preliminarily determined. In this case, a possibility that the liquid to be measured overflows from the opening can be eliminated without carrying out a particular detection method.

Furthermore, it should be appreciated that the present invention is not limited to the above-described embodiments, but can be variously modified without departing from the scope thereof.

REFERENCE CHARACTERS LIST

20: Cartridge
26: Liquid sample flow path (Measuring flow path)
261: Inner wall surface
262: Inner wall surface facing stepwise concave portion
7: Stepwise concave portion
28c, 29c: Detecting electrode
T: Projection part
T1: Downstream side edge
40: Base material
42: Concave groove
50: Adhesive sheet
60: Film
601: Adhesion surface of the film

The invention claimed is:

1. A liquid sample analyzer comprising:
    a liquid sample flow path for flowing a liquid sample;
    a detection part contained and arranged in a stepwise concave portion formed on an inner wall surface of the liquid sample flow path; and
    a projection part provided at a position facing the stepwise concave portion on the inner wall surface of the liquid sample flow path, and configured to generate a turbulent flow on a front side of an opening of the stepwise concave portion, wherein
    the projection part is formed so that a downstream side edge at the top part can be positioned upstream of the downstream side edge of the detection part.

2. The liquid sample analyzer according to claim 1, wherein
    the projection part is formed on a wall surface facing the stepwise concave portion in the inner wall surface of the liquid sample flow path.

3. The liquid sample analyzer according to claim 2, comprising:
    a base material forming a concave groove on the inner wall surface; and
    a film adhered to a surface of the base material by an adhesive layer, for blocking the concave groove together with the adhesive layer to form the liquid sample flow path, wherein
    the detection part is arranged on an adhesive surface of the film, and the stepwise concave portion is formed by the adhesive layer and the adhesive surface of the film.

4. The liquid sample analyzer according to claim 1, comprising:
    a base material forming a concave groove on the inner wall surface; and
    a film adhered to a surface of the base material by an adhesive layer, for blocking the concave groove together with the adhesive layer to form the liquid sample flow path, wherein
    the detection part is arranged on an adhesive surface of the film, and the stepwise concave portion is formed by the adhesive layer and the adhesive surface of the film.

* * * * *